(12) United States Patent
Cottrell et al.

(10) Patent No.: US 7,855,231 B2
(45) Date of Patent: *Dec. 21, 2010

(54) HIGH CONCENTRATION TOPICAL INSECTICIDE CONTAINING INSECT GROWTH REGULATOR

(75) Inventors: Ian W. Cottrell, Spring Hill, FL (US); Albert Ahn, Short Hills, NJ (US); Linda Dorneval, Bloomfield, NJ (US)

(73) Assignee: Summit VetPharm, LLC, Rutherford, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/741,638

(22) Filed: Apr. 27, 2007

(65) Prior Publication Data

US 2007/0254927 A1 Nov. 1, 2007

Related U.S. Application Data

(60) Provisional application No. 60/795,674, filed on Apr. 28, 2006.

(51) Int. Cl.
*A01N 43/08* (2006.01)
(52) U.S. Cl. .................. 514/534; 514/471; 514/772
(58) Field of Classification Search .................. None
See application file for complete search history.

(56) References Cited

U.S. PATENT DOCUMENTS

| | | | |
|---|---|---|---|
| 5,283,229 A | 2/1994 | Narayanan | |
| 5,434,181 A | 7/1995 | Kodaka | |
| 5,532,365 A | 7/1996 | Kodaka | |
| 6,479,542 B2 | 11/2002 | Sembo et al. | |
| 6,867,223 B2 * | 3/2005 | Cottrell et al. | 514/345 |
| 6,984,662 B2 | 1/2006 | Cottrell | |
| 7,132,448 B2 | 11/2006 | Cottrell | |
| 7,195,773 B2 | 3/2007 | Morita et al. | |
| 2002/0103233 A1 * | 8/2002 | Arther | 514/341 |
| 2004/0157743 A1 * | 8/2004 | Rosenfeldt et al. | 504/253 |
| 2005/0096386 A1 * | 5/2005 | Cottrell et al. | 514/471 |
| 2007/0037001 A1 | 2/2007 | Gao et al. | |
| 2007/0142439 A1 | 6/2007 | Morita et al. | |

FOREIGN PATENT DOCUMENTS

| | | |
|---|---|---|
| CA | 2498183 | 3/2004 |
| CA | 2543081 | 8/2004 |
| CA | 2533467 | 2/2005 |
| CA | 2579844 | 4/2006 |
| WO | 91/04965 | 4/1991 |
| WO | 93/24004 | 12/1993 |

OTHER PUBLICATIONS

International Search Report and Written Opinion of the International Searching Authority for International Application No. PCT/US07/67703 dated Sep. 2, 2008.
Office Action mailed on Jul. 22, 2010, for Canadian Patent Application No. 2,650,815, filed on Apr. 27, 2007.

* cited by examiner

*Primary Examiner*—Robert A Wax
*Assistant Examiner*—Melissa S Mercier
(74) *Attorney, Agent, or Firm*—Stroock & Stroock & Lavan LLP

(57) ABSTRACT

A topical insecticide is provided which can be safe to use and avoids many common deleterious side effects of conventional topical insecticides. The insecticide contains an insecticide and an insect growth regulator effective for killing fleas, flea larvae and flea eggs. The insecticide is formulated by dissolving an insecticidal (tetrahydro-3-furanyl) methylamine derivative and an insect growth regulator (IGR) in a solvent containing N-octyl pyrrolidone and/or N-methyl pyrrolidone to increase the solvency of the IGR component, thereby providing an insecticide having high insecticidal activity.

9 Claims, No Drawings

HIGH CONCENTRATION TOPICAL INSECTICIDE CONTAINING INSECT GROWTH REGULATOR

CROSS REFERENCE TO RELATED APPLICATIONS

The present application claims the benefit of U.S. Provisional Application No. 60/795,674, filed Apr. 28, 2006. Priority is claimed to the application listed above, which is incorporated herein by reference.

BACKGROUND OF INVENTION

The invention relates generally to insecticides and more particularly to a topical insecticide, such as one suitable to use on house pets such as cats and dogs.

The infestation of animals with fleas is highly undesirable. Accordingly, it has become common to administer both topical and internal insecticides to livestock and pets. Topical applications can be desirable, in that many insecticides are acceptably safe when used topically, but not when used internally.

Various topical insecticides have drawbacks. Some require a large volume to be applied to the animal. This can cause considerable mess and can lead to an unpleasant smell. Also, when the animal is a house pet, there is a further complication in that the insecticide should be safe for human contact. It should also not lead to staining of furniture, carpeting and the like. Finally, even if safe, topical insecticides for house pets should not be irritating or lead to rashes, hair loss or exhibit other unpleasant side effects.

Accordingly, it is desirable to provide an improved topical insecticide, which overcomes drawbacks of the prior art.

SUMMARY OF THE INVENTION

Generally speaking, in accordance with the invention, a topical insecticide is provided which includes an insecticide in combination with an insect growth regulator. These ingredients are advantageously dissolved to a high concentration in a solution containing a quaternary ammonium salt, such as cetyltrimethylammonium chloride, tallowalkyltrimethylammonium chloride, or oleyldimethylammonium chloride. The insecticide formulation of the invention can be safe to use and avoids many common deleterious side effects of conventional topical insecticides. Accordingly, provided is an improved topical insecticide that overcomes drawbacks of the prior art, a method of preparing an insecticide and a method of controlling infestation with an insecticide.

The invention provides a topical insecticide that contains an insecticide and an insect growth regulator, which is advantageously effective to kill fleas, flea eggs, and flea larvae. The insecticide component preferably contains an insecticidal (tetrahydro-3-furanyl) methylamine derivative or a chloronicotinyl insecticide. It advantageously also includes an insect growth regulator (IGR) in a solvent component. Advantageous solvent solutions include those that contain water, ethyl lactate and/or a quaternary ammonium salt. The quaternary ammonium salt is preferably a hydrophobic ammonium salt such as oleyldimethylammonium chloride, tallowalkyltrimethylammonium chloride, and oleyldimethylammonium chloride.

It has been determined that an ammonium chloride with large numbers of carbon atoms, preferably about 16 or more, results in a more favorable solvent system. In a preferred embodiment of the invention, the solvent component advantageously contains a sufficient amount of the salt to increase the solvency of the IGR compared to the solvency of the IGR in the solvent without the salt. The selection of components in the solvent system allows for increased solubility of the insecticide and insect growth regulator thereby providing an insecticide having high insecticidal activity.

Active ingredients and insecticides in accordance with preferred embodiments of the invention are generally available as crystals and other solids. It has been determined that it is advantageous to dissolve or otherwise put these actives into a liquid form (e.g., mixture, emulsion, slurry, etc.) for use as topical spot products on animals. Topical spot products are more advantageous if the amount of liquid applied can be minimized. This should be balanced with the need for appropriate dosage to achieve the desired insecticidal effect. Therefore, it is desirable to use a solvent that will allow the solubilization of a high concentration of insecticide.

In a preferred embodiment of the invention, the insecticide contains 1-{(tetrahydro-3-furanyl)methyl}-2-nitro-3-methylguanidine (dinotefuran) and the IGR comprises pyriproxyfen and/or methoprene. In another preferred embodiment of the invention, the insecticide comprises a chloronicotinyl insecticide, preferably acetamiprid, imidacloprid, nitenpyram or clothianidin, and the IGR comprises pyriproxfen and/or methoprene.

Dinotefuran is an insecticide that kills adult fleas, and pyriproxyfen and methoprene are insect growth regulators that kill flea larvae and prevent flea eggs from hatching. Accordingly, the combination of an insecticide, such as acetamiprid or dinotefuran and an IGR, such as pyriproxyfen or methoprene, provides for an effective flea control system since only about 5% of the existing fleas on an animal are adults and the other 95% are in a juvenile state (eggs and larvae).

Dinotefuran and pyriproxyfen are hydrophilic and lipophilic, respectively. A solvent system that provides for solubilization of a high concentration of dinotefuran will typically not allow pyriproxyfen to solubilize. However, it has been determined that the addition of a quaternary ammonium salt such as cetyltrimethylammonium chloride, tallowalkyltrimethyl ammonium chloride, and oleyldimethylammonium chloride allows for an effective amount of pyriproxyfen to solubilize. Moreover, the salt can help prevent emulsification of the formulation. This advantageously produces an insecticide with high insecticidal activity.

Accordingly, it is an object of the invention to provide an improved topical insecticide.

Another object of the invention is to provide a method for controlling insect infestation.

Another object of the invention is to provide a topical insecticide that works more rapidly and/or more permanently than other insecticides and/or can include a lower total volume of insecticide applied.

Another object of the invention is to provide an improved method of making an insecticide.

Other objects and features will be in part apparent and in part pointed out.

DETAILED DESCRIPTION OF THE PREFERRED EMBODIMENTS

In accordance with the invention, topical insecticide formulations, which contain an insecticide and an insect growth regulator effective to kill fleas, flea eggs, and flea larvae are provided. Combining an insecticide effective against adult fleas with an insect growth regulator effective against flea eggs and larvae results in a highly effective insecticidal formulation.

In one preferred embodiment of the invention, the insecticide is formulated by dissolving an insecticidal (tetrahydro-3-furanyl) methylamine derivative and an insect growth regulator (IGR) in a solvent component comprising water, ethyl lactate and quaternary ammonium salt. The solvent component contains a sufficient amount of quaternary ammonium salt to increase the solvency of the IGR compared to the solvency of the IGR in the solvent without the quaternary ammonium salt and to increase the effectiveness of the insecticide compared to its effectiveness without the quaternary ammonium salt.

In a preferred embodiment of the invention, the active ingredient of the insecticide formulation is an amine derivative, having a nitro-methylene group, a nitroamino group or a cyanoamino group, which can be formulated to have low toxicity and excellent insecticidal activity. Active ingredients of insecticides and their method of formation in accordance with the preferred embodiments of the invention are discussed in U.S. Pat. Nos. 5,532,365; 5,434,181; 6,867,223; 6,984,662 and 7,132,448 the contents of which are incorporated herein by reference.

In another preferred embodiment of the invention, the insecticide comprises an insecticidal (tetrahydro-3-furanyl) methylamine derivative of the following formula (1). The (tetrahydro-3-furanyl)methylamine derivatives of the formula (1) have an excellent insecticidal activity even in the absence of a pyridylmethyl group or a thiazolylmethyl group in their molecular structure.

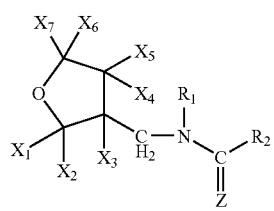

(1)

where $X_1, X_2, X_3, X_4, X_5, X_6$ and $X_7$ each represent each a hydrogen atom or a alkyl group having from 1 to 4 carbon atoms; $R_1$ represents a hydrogen atom, an alkyl group having from 1 to 5 carbon atoms, an alkenyl group having 3 carbon atoms, a benzyl group, an alkoxyalkyl group having from 2 to 4 carbon atoms (in its whole group), an alkyloxycarbonyl group having from 1 to 3 carbon atoms, a phenoxy carbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group or an N,N-dimethylcarbamoyl group; $R_2$ represents a hydrogen atom, an amino group, a methyl group, an alkylamino group having from 1 to 5 carbon atoms, a di-substituted alkylamino group having from 2 to 5 carbon atoms (in its whole group), a 1-pyrrolidinyl group, an alkenylamino group having 3 carbon atoms, an alkynylamino group having 3 carbon atoms, a methoxyamino group, an alkoxyalkylamino group having from 2 to 4 carbon atoms (in its whole group), a methylthio group or $-N(Y_1)Y_2$ (where $Y_1$ represents an alkyloxycarbonyl group having from 1 to 3 carbon atoms, a phenoxycarbonyl group, an alkylcarbonyl group having from 1 to 6 carbon atoms, an alkenylcarbonyl group having from 2 to 3 carbon atoms, a cycloalkylcarbonyl group having from 3 to 6 carbon atoms, a benzoyl group, a benzoyl group substituted by alkyl group(s) having from 1 to 4 carbon atoms, a benzoyl group substituted by halogen atom(s), a 2-furanylcarbonyl group, an N,N-dimethylcarbamoyl group, a (tetrahydro-3-furanyl) methyl group or a benzyl group, and $Y_2$ represents a hydrogen atom or an alkyl group having from 1 to 5 carbon atoms); and Z represents $=N-NO_2$, $=CH-NO_2$ or $=N-CN$.

Intermediates for producing the compounds of the formula (1) are represented by a formula (2):

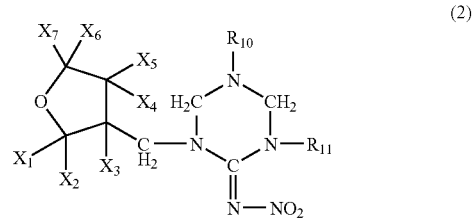

(2)

where $X_1, X_2, X_3, X_4, X_5, X_6$ and $X_7$ each represent each a hydrogen atom or an alkyl group having from 1 to 4 carbon atoms; $R_{10}$ represents an alkyl group having from 1 to 5 carbon atoms or a benzyl group; and $R_{11}$ represents an alkyl group having from 1 to 5 carbon atoms or a benzyl group.

The (tetrahydro-3-furanyl)methylamine derivatives of the formula (1) and formula (2) according to the invention are excellent compounds having a high insecticidal activity and broad insecticidal spectrum. Further, agricultural chemicals containing the (tetrahydro-3-furanyl)methylamine derivatives of the formula (1) and (2) according to the invention have outstanding characteristics as insecticides and hence are useful.

Specific examples of the alkyl group for $X_1, X_2, X_3, X_4, X_5, X_6$ and $X_7$ in the above formulae (1) and (2) include a methyl group, an ethyl group, an n-propyl group, an iso-propyl group, a tert-butyl group, and the like, preferably a methyl group.

Specific examples of the alkyl group for $R_1$ include a methyl group, an ethyl group, an n-propyl group, an iso-propyl group, an n-butyl group, an iso-butyl group, a sec-butyl group, a tert-butyl group, an n-pentyl group, and the like.

Specific examples of the alkenyl group for $R_1$ include a 1-propenyl group, a 2-propenyl group, and the like.

Specific examples of the alkoxyalkyl group for $R_1$ include a methoxymethyl group, an ethoxymethyl group, an n-propoxymethyl group, an iso-propoxymethyl group, a methoxyethyl group, an ethoxyethyl group, and the like.

Specific examples of the alkyloxycarbonyl group for $R_1$ include a methyloxycarbonyl group, an ethyloxycarbonyl group, an n-propyloxycarbonyl group, an iso-propyloxycarbonyl group, and the like.

Specific examples of the alkylcarbonyl group for $R_1$ include a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group, a tert-butylcarbonyl group, an n-pentylcarbonyl group, an n-hexylcarbonyl group, and the like.

Specific examples of the alkenylcarbonyl group for R1 include a vinylcarbonyl group, a 1-methylvinylcarbonyl group, and the like.

Specific examples of the cycloalkylcarbonyl group for $R_1$ include a cyclopropylcarbonyl group, a cyclobutylcarbonyl group, a cyclopentylcarbonyl group, a cyclohexylcarbonyl group, and the like.

Specific examples of the benzoyl group substituted by alkyl group(s) for $R_1$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) for R1 include a 2-chlorobenzoyl group, a 3-chlorobenzoyl group, a 4-chlorobenzoyl group, a 3,4-dichloro-benzoyl group, a 4-fluorobenzoyl group, and the like.

Although $R_1$ can take various substituents as described above, it is preferably a hydrogen atom, an alkylcarbonyl group having from 1 to 4 carbon atoms or a cyclopropylcarbonyl group.

Specific examples of the alkylamino group for $R_2$ include a methylamino group, an ethylamino group, an n-propyl-amino group, an iso-propylamino group, an n-butylamino group, an iso-butylamino group, a sec-butylamino group, a tert-butylamino group, an n-pentylamino group, and the like, preferably a methylamino group.

Specific examples of the di-substituted alkylamino group for $R_2$ include a dimethylamino group, a diethylamino group, an N-methyl-N-ethylamino group, an N-methyl-N-n-propylamino group, an N-methyl-N-n-butylamino group, and the like, preferably a dimethylamino group.

Specific examples of the alkenylamino group for $R_2$ include a 1-propenylamino group, a 2-propenylamino group, and the like.

Specific examples of the alkynylamino group for $R_2$ include a propargylamino group, and the like.

Specific examples of the alkoxyalkylamino group for $R_2$ include a methoxymethylamino group, an ethoxymethylamino group, an n-propoxymethylamino group, an iso-propoxymethylamino group, a methoxyethylamino group, an ethoxyethylamino group, and the like.

Specific examples of the alkyloxycarbonyl group denoted by $Y_1$ for $R_2$ include a methyloxycarbonyl group, an ethyloxy-carbonyl group, an n-propyloxycarbonyl group, an iso-propyloxy-carbonyl group, and the like.

Specific examples of the alkylcarbonyl group denoted by $Y_1$ for $R_2$ include a methylcarbonyl group, an ethylcarbonyl group, an n-propylcarbonyl group, an iso-propylcarbonyl group, an n-butylcarbonyl group, an isobutylcarbonyl group, a sec-butyl-carbonyl group, a tertbutylcarbonyl group, an n-pentylcarbonyl group, an n-hexylcarbonyl group, and the like, preferably a methylcarbonyl group, an ethylcarbonyl group, an n-propylcarbonyl group, an iso-propylcarbonyl group, an n-butylcarbonyl group, an iso-butylcarbonyl group, a sec-butylcarbonyl group and a tert-butylcarbonyl group.

Specific examples of the alkenylcarbonyl group denoted by $Y_1$ for $R_2$ include a vinylcarbonyl group, a 1-methyl-vinyl-carbonyl group, and the like.

Specific examples of the cycloalkylcarbonyl group denoted by $Y_1$ for $R_2$ include a cyclopropylcarbonyl group, a cyclobutylcarbonyl group, a cyclopentylcarbonyl group, a cyclo-hexylcarbonyl group, and the like, preferably a cyclopropyl-carbonyl group.

Specific examples of the benzoyl group substituted by alkyl group(s) denoted by $Y_1$ for $R_2$ include a 2-methylbenzoyl group, a 3-methylbenzoyl group, a 4-methylbenzoyl group, a 4-tert-butylbenzoyl group, and the like.

Specific examples of the benzoyl group substituted by halogen atom(s) denoted by $Y_1$ for $R_2$ include a 2-chlorobenzoyl group, a 3-chlorobenzoyl group, a 4-chlorobenzoyl group, a 3,4-dichlorobenzoyl group, a 4-fluoro benzoyl group, and the like.

Specific examples of the alkyl group denoted by $Y_2$ for $R_2$ include a methyl group, an ethyl group, an n-propyl group, an iso-propyl group, an n-butyl group, an iso-butyl group, a sec-butyl group, a tert-butyl group, an n-pentyl group, and the like, preferably a methyl group.

In the formula (1), compounds in which $R_1$ and $Y_1$ are concurrently an alkylcarbonyl group having from 1 to 4 carbon atoms or a cyclopropylcarbonyl group are preferred from the viewpoint of both insecticidal activity and production method.

In a preferred embodiment of the invention, the (tetrahydro-3-furanyl)methylamine derivative dissolved in the solvent component is dinotefuran. Dinotefuran is an insecticide that will kill adult fleas. Preferably, dinotefuran is dissolved in the formulation to a concentration range of about 5 to 20%, more preferably about 10 to 15%, and most preferably about 12 to 15%. All percentages, unless otherwise evident, are on a weight basis.

In another preferred embodiment of the invention, the insecticide is formulated by dissolving an insecticidally effective amount of a chloronicotinyl insecticide and an insect growth regulator (IGR) in a solvent component. The solvent component contains a sufficient amount of quaternary ammonium salt to increase the solvency of the IGR compared to the solvency of the IGR in the solvent without the quaternary ammonium salt and to increase the effectiveness of the insecticide compared to its effectiveness without the quaternary ammonium salt. In a preferred embodiment of the invention, the solvent component comprises ethanol and a quaternary ammonium salt. In another preferred embodiment of the invention, the solvent component comprises water, ethyl lactate and a quaternary ammonium salt.

In a preferred embodiment of the invention, the chloronicotinyl insecticide in the formulation is N-((6-chloro-3-pyridinyl)methyl)-N'-cyano-N-methyl-ethanimidamide (acetamiprid) and the insect growth regulator is pyriproxfen or methoprene. Acetamiprid is an insecticide that primarily kills adult fleas. Acetamiprid is disclosed in international applications PCT/JP90/01282 and PCT/EP93/01286, the contents of which are disclosed herein by reference.

In another preferred embodiment of the invention, the insect growth regulator is pyriproxyfen. In a preferred embodiment of the invention, pyriproxyfen is dissolved in the formulation to a concentration range of about 0.1 to 3%, more preferably about 0.5 to 3% and most preferably about 0.9 to 1.1%. In another preferred embodiment of the invention, the formulation comprises a dosage of at least about 10 mg of pyriproxyfen to an animal. Therefore, if the formulation contains 1% pyriproxyfen, an acceptable dosage would be about 10 mg or more in a 1 ml application.

In yet another preferred embodiment of the invention, the insect growth regulator is methoprene. In a preferred embodiment of the invention, methoprene is dissolved in the formulation to a concentration range of about 0.1 to 5%, more preferably about 0.5 to 5%, and most preferably about 3.0 to 5.0%. In another preferred embodiment of the invention, the dosage comprises at least about 30 mg of methoprene administered to the animal.

In one preferred embodiment of the invention, the insecticide is formulated by dissolving dinotefuran and pyriproxyfen in a solvent comprising water, ethyl lactate and a quaternary ammonium salt, preferably oleyldimethylammonium chloride. In another preferred embodiment of the invention, the insecticide is formulated by dissolving dinotefuran and pyriproxyfen in a solvent comprising ethanol and a quaternary ammonium salt, preferably oleyldimethylammonium chloride. Dinotefuran is an insecticide which kills adult fleas, acetamiprid is an insecticide that primarily kills adult fleas, and pyriproxyfen is an insecticide which kills flea larvae and flea eggs. By killing fleas in the adult and juvenile stages, the insecticide formulation of the invention is useful to improve the speed of result and decrease the reoccurrence of flea infestation compared to other insecticide formulations.

In another preferred embodiment of the invention, the insecticide is formulated by dissolving acetamiprid and pyriproxyfen in a solvent preferably comprising water, ethyl lactate and a quaternary ammonium salt, preferably oleyldimethylammonium chloride. In yet another preferred embodiment of the invention, the insecticide is formulated by dissolving acetamiprid and pyriproxyfen in a solvent preferably comprising ethanol and a quaternary ammonium salt, preferably oleyldimethylammonium chloride. Acetamiprid is an insecticide that primarily kills adult fleas, and pyriproxyfen is an insecticide which kills flea larvae and flea eggs. By killing fleas in the adult and juvenile stages, the insecticide formulation of the invention is useful to improve the speed of result and decrease the reoccurrence of flea infestation compared to other insecticide formulations.

High concentrations of dinotefuran and acetamiprid can be solubilized in a combination of water and ethyl lactate or ethanol. However, because dinotefuran is hydrophilic and pyriproxyfen is lipophilic, a solvent system which provides for solubilization of a high concentration of dinotefuran will not allow pyriproxyfen to solubilize properly. It has been determined that the addition of a quaternary ammonium salt such as an ammonium chloride, preferably with one or more carbon atoms, for example, cetyltrimethylammonium chloride, tallowalkyltrimethyl ammonium chloride and oleyldimethylammonium chloride, to the solvent component allows for an effective amount of pyriproxyfen to solubilize into the formulation without emulsification, thereby allowing for the delivery of high concentrations of hydrophilic and lipophilic insecticides in a single highly effective insecticidal topical solution.

Because pyriproxyfen is hydrophobic, it may be preferable to select a quaternary ammonium salt that is also hydrophobic in order to dissolve an effective amount pyriproxyfen into the insecticide formulation. Quaternary ammonium salts having a high number of carbon atoms in the alkyl chains such as cetyltrimethylammonium chloride, tallowalkyltrimethyl ammonium chloride and oleyldimethylammonium chloride, are preferably selected for use in the solvent component. Preferably, insecticidally effective amounts of dinotefuran and pyriproxyfen are incorporated into relatively low volumes. Such insecticide formulations are advantageously stable under various conditions of high and low temperature.

In another preferred embodiment of the invention, the preferred solvent component comprises a mixture comprising water, ethyl lactate and oleyldimethylammonium chloride, wherein the final concentration of oleyldimethylammonium chloride ranges from 0.5 to 20%, more preferably 0.5 to 5% oleyldimethylammonium chloride, and most preferably a final concentration of 1.0% oleyldimethylammonium chloride. When the solvent contains oleyldimethylammonium chloride, the ratio of water to ethyl lactate in the solvent is preferably approximately about 1:1 to 1:2.

Ethanol can also be added to the solvent component to improve solubility and to prevent high concentrations of dinotefuran or acetamiprid from crystallizing over time at low temperatures. In another preferred embodiment of the invention, the preferred solvent component comprises a mixture comprising water, ethyl lactate, ethanol and oleyldimethylammonium chloride, wherein the final concentration of oleyldimethylammonium chloride ranges from 0.5 to 20%, more preferably 0.5 to 5% oleyldimethylammonium chloride, and most preferably a final concentration of 1.0% oleyldimethylammonium chloride. When the solvent contains oleyldimethylammonium chloride, the ratio of water to ethyl lactate to ethanol in the solvent is preferably approximately about 1:1:1 to about 3:4:3, and all ratios in between. All ratios, unless otherwise evident, are on a weight basis.

In a preferred embodiment of the invention, the insecticide is formulated by dissolving dinotefuran and pyriproxyfen in a solvent comprising water, ethyl lactate and one of the above salts, such as oleyldimethylammonium chloride. Dinotefuran is dissolved in the formulation to a concentration range of about 5 to 20%, pyriproxyfen is dissolved in the formulation to a concentration range of about 0.5 to 3%, the concentration of oleyldimethylammonium chloride ranges from about 1 to 20%, and the concentration of ethyl lactate ranges from about 50 to 67%. Preferably, dinotefuran is dissolved in the formulation to a concentration of about 15%, pyriproxyfen is dissolved in the formulation to a concentration of about 1%, and the concentration of oleyldimethylammonium chloride is about 1%.

When the insecticide is formulated by dissolving dinotefuran and pyriproxyfen in a solvent comprising water, ethyl lactate and oleyldimethylammonium chloride, the ratio of dinotefuran to pyriproxyfen to oleyldimethylammonium chloride is preferably about 15:1:1, and the concentration of dinotefuran in the insecticide formulation does not exceed 15%. In other preferred embodiments, the ratio of dinotefuran to pyriproxyfen to oleyldimethylammonium chloride is preferably approximately about 10:1:1, 20:1:1 or 30:1:1 and all ratios in between, and the concentration of dinotefuran preferably does not exceed 15%.

For the application of about 0.5 to 1.33 ml of the insecticide to a companion animal weighing 9 pounds or less, it is preferable that the insecticide is formulated by dissolving approximately 150-200 mg of dinotefuran and approximately 10 mg of pyriproxyfen in a solvent comprising water, ethyl lactate and oleyldimethylammonium chloride to achieve a 90% kill rate for fleas.

In yet another embodiment of the invention, the preferred solvent component comprises a mixture comprising water, ethyl lactate and cetyltrimethylammonium chloride, wherein the final concentration of cetyltrimethylammonium chloride is approximately 19 to 20%, and more preferably, the final concentration of cetyltrimethylammonium chloride is approximately 20%. Ethanol can also be added to the solvent component to improve solubility.

Preferably, when the insecticide is formulated by dissolving dinotefuran and pyriproxyfen in a solvent comprising water, ethyl lactate and cetyltrimethylammonium chloride, dinotefuran is dissolved in the formulation to a concentration range of about 14 to 15%, pyriproxyfen is dissolved in the formulation to a concentration range of about 1 to 3%, the concentration of cetyltrimethylammonium chloride ranges from about 19 to 20%, and the concentration of ethyl lactate ranges from about 40 to 75%.

In yet another embodiment of the invention, the preferred solvent component comprises a mixture comprising water, ethyl lactate and tallowalkyltrimethyl ammonium chloride, wherein the final concentration of tallowalkyltrimethyl ammonium chloride ranges from approximately 19 to 20%, and more preferably, the final concentration of tallowalkyltrimethyl ammonium chloride is about 20%. Ethanol can also be added to the solvent component to improve solubility.

Preferably, when the insecticide is formulated by dissolving dinotefuran and pyriproxyfen in a solvent comprising water, ethyl lactate and tallowalkyltrimethyl ammonium chloride, dinotefuran is dissolved in the formulation to a concentration range of about 14 to 15%, pyriproxyfen is dissolved in the formulation to a concentration range of about 1 to 3%, the concentration of tallowalkyltrimethyl ammonium chloride ranges from about 19 to 20%, and the concentration of ethyl lactate ranges from about 40 to 75%.

In another embodiment of the invention, the insecticide is formulated by dissolving acetamiprid and pyriproxfen in a solvent comprising water, ethyl lactate and a quaternary ammonium salt such as cetyltrimethylammonium chloride, tallowalkyltrimethyl ammonium chloride and oleyldimethylammonium chloride. Acetamiprid is dissolved in the formulation to a concentration range of about 5 to 50%, pyriproxfen is dissolved in the formulation to a concentration range of about 0.5 to 3%, the concentration of the quaternary ammonium salt ranges from about 1 to 20%, and the concentration of ethyl lactate ranges from about 50 to 67%.

For the application of about 0.4 to 1.33 ml of the insecticide to a companion animal weighing 9 pounds or less, it is preferable that the insecticide is formulated by dissolving approximately 100 mg/ml of acetamiprid and approximately 10 mg/ml of pyriproxyfen in a solvent comprising water, ethyl lactate, ethanol and oleyldimethylammonium chloride to achieve a 90% kill rate for fleas.

Solvent Containing N-octyl Pyrrolidone and/or N-Methyl Pyrrolidone

In accordance with another preferred embodiment of the invention, the preferred solvent includes N-octyl pyrrolidone (NOP) and/or N-methyl pyrrolidone (NMP). The inventors determined that N-octyl pyrrolidone and N-methyl pyrrolidone, either alone or in combination, can increase the degree of dissolution of the insecticide components, more specifically, dinotefuran. The greater amount of dissolution can enhance efficiency of the insecticide composition by requiring less solvent to dissolve the same amount of insecticide compositions, increasing insecticide concentration and leading to lower volumes of material to be applied to the animal.

Preferably, the insecticide comprises N-octyl pyrrolidone in a concentration range of approximately 0-10%, more preferably approximately 5-7%, most preferably about 6%. Additionally, the insecticide can comprise N-methyl pyrrolidone in a concentration range of approximately 45-94%. Preferably, the insecticide comprises dinotefuran in a concentration range of approximately 5-40%, and pyriproxyfen in a concentration range of approximately 1 to 7%. All percentages, unless otherwise specified, are on a weight basis.

Formulation A: In one exemplary embodiment of the invention, the insecticide comprises dinotefuran in a concentration range of about 5-30%, pyriproxyfen in a concentration range of about 1-3%, N-octyl pyrrolidone in a concentration range of approximately 0.1-6% and N-methyl pyrrolidone in a concentration range of approximately 61-94%. All percentages, unless otherwise specified, are on a weight basis.

Formulation B: In one exemplary embodiment of the invention, the insecticide comprises dinotefliran in a concentration range of about 20-40%, pyriproxyfen in a concentration of about 1%, N-octyl pyrrolidone in a concentration of approximately 6% and N-methyl pyrrolidone in a concentration range of approximately 53-73%. All percentages, unless otherwise specified, are on a weight basis.

Formulation C: In one exemplary embodiment of the invention, the insecticide comprises dinotefuran in a concentration of about 30%, pyriproxyfen in a concentration range of about 1.5-7%, N-octyl pyrrolidone in a concentration of approximately 6% and N-methyl pyrrolidone in a concentration range of approximately 57-63%. All percentages, unless otherwise specified, are on a weight basis.

Formulation D: In one exemplary embodiment of the invention, the insecticide comprises dinotefuran in a concentration of about 35%, pyriproxyfen in a concentration range of about 1.5-7%, N-octyl pyrrolidone in a concentration of approximately 6% and N-methyl pyrrolidone in a concentration range of approximately 52-58%. All percentages, unless otherwise specified, are on a weight basis.

Formulation E: In one exemplary embodiment of the invention, the insecticide comprises dinotefuran in a concentration range of about 20-25%, pyriproxyfen in a concentration of about 2%, N-octyl pyrrolidone in a concentration of approximately 6%, N-methyl pyrrolidone in a concentration range of approximately 45-54% and water in a concentration of about 16-27%. All percentages, unless otherwise specified, are on a weight basis.

Formulation F: In one exemplary embodiment of the invention, the insecticide comprises dinotefuran in a concentration of about 35%, pyriproxyfen in a concentration of about 5%, N-octyl pyrrolidone in a concentration of approximately 6% and N-methyl pyrrolidone in a concentration of approximately 54%. All percentages, unless otherwise specified, are on a weight basis.

Formulation G: In one exemplary embodiment of the invention, the insecticide comprises dinotefuran in a concentration range of about 18-26%, pyriproxyfen in a concentration range of about 2-4%, N-octyl pyrrolidone in a concentration range of approximately 3-8%, N-methyl pyrrolidone in a concentration range of approximately 30-48% and propylene carbonate in a concentration range of approximately 30-38%. All percentages, unless otherwise specified, are on a weight basis.

Formulation H: In one exemplary embodiment of the invention, the insecticide comprises dinotefuran in a concentration of about 22%, pyriproxyfen in a concentration of about 3%, N-octyl pyrrolidone in a concentration of approximately 6%, N-methyl pyrrolidone in a concentration of approximately 34.74% and propylene carbonate in a concentration of approximately 34%. All percentages, unless otherwise specified, are on a weight basis.

In the preparation of a formulation in accordance with the invention for use on companion animals, there are several parameters that should be considered. These are:

(a) Concentration high enough to minimize the volume of the topical applied to the animal (one would not want to put 20 ml, e.g., onto a small cat).
(b) The formulation should be stable for one month at 130° F., 110° F., 40° F., room temperature and 0° F. This helps ensure that the formulation remains stable under the conditions that it could meet in commerce.
(c) Safe to use on the animal—particularly non-irritating since the product is applied to the skin. Also safe if ingested by the animal; ingestion can occur when cats groom themselves.
(d) Safe to use by the consumer.
(e) Efficacious in use—should kill greater than 80% or even 90% of the fleas up to 28 days.
(f) Efficacy would be reduced if crystallization occurred in the package.
(g) Needs to be aesthetically pleasing—"no oily drop" on the animal when applied.

(h) Fast drying to reduce the chance of the animal shaking off the liquid thereby reducing efficacy.
(i) Microbiologically stable.

Other additives to the insecticidal formulation can include, but are not limited to, fragrances to improve odor and surfactants such as isopropyl myristate and sorbitan derivatives such as polysorbate 20 and spreading agents to increase performance. Polymers may also be used to provide enrobing of the insecticide to improve safety and adhesion to skin and hair. Examples of polymers that may be used include cationic cellulose, cationic guar, cationic acrylate polymers, agar, gelatin and alginate.

In practice, an effective amount of the insecticidal formulation as described herein may be applied to a companion animal, preferably a dog or cat, as a foaming shampoo, dip, aerosol spray, pump spray, lotion, emulsifiable concentrate, aqueous or liquid flowable, suspension concentrate and by any other methods suitable for administering topical compositions to animals.

In a preferred embodiment of the invention, the insecticidal formulation can be applied as a topical drop about once a month, preferably in the area between the shoulder blades and the base of the skull to kill fleas, flea larvae and flea eggs over a one-month period.

The following examples are given for purposes of illustration only and are not intended to be construed in a limiting manner.

EXAMPLES

Example 1

Preparation of 1-{(tetrahydro-3-furanyl)methyl}-2-nitro-3-methylguanidine(dinotefuran)

A mixture comprising 10.0 g of (tetrahydro-3-furanyl) methanol, 29.5 g of trifluoromethanesulfonic anhydride, 10.0 g of pyridine and 200 ml of dichloromethane was stirred for an hour at room temperature. Water was poured into the reaction solution to separate the organic layer, which was washed with 1 N hydrochloric acid, water and a saturated saline solution, dried, and concentrated to obtain 20 g of 3-tetrahydro-furanylmethyl triflate. 3.25 g of 60% sodium hydride were added to 12.5 g of 1,5-dimethyl-2-nitroimino-hexahydro-1,3,5-triazine and 60 ml of DMF at room temperature, followed by stirring for an hour. 20.0 g of the 3-tetrahydrofuranylmethyl triflate were added thereto, and the mixture was stirred at 50° C. for 2 hours. After cooling the mixture to room temperature, 50 ml of 2N hydrochloric acid were added thereto, followed by stirring at 50° C. for 2 hours. The resultant mixture was neutralized with sodium bicarbonate and extracted with dichloromethane, and the extract was dried and concentrated. The residue thus obtained was purified by silica gel column chromatography (eluent: ethyl acetate/hexane=1/1) to obtain 7.8 g of 1-{(tetrahydro-3-furanyl)methyl}-2-nitro-3-methylguanidine (dinotefuran).

Example 2

Preparation of Insecticide Formulation Containing Dinotefuran, Pyriproxyfen, and Oleyldimethylammonium Chloride 0.5 g of oleyldimethylammonium chloride was added to 0.5 g of pyriproxyfen with heat (50 degrees C.) and dissolved. 20.75 g of water followed by 20.75 g of ethyl lactate was then added. 2.1 g of t-octylphenoxypolyethoxyethanol containing 9 moles of ethlyene oxide (OP 9) was added. 7.8 g of dinotefuran was dissolved in the solution by stirring to produce a clear homogeneous solution followed by cooling to room temperature. The pH was adjusted with sodium carbonate solution to between 5.5 and 7.

Example 3

Stability of Dinotefuran/Pyriproxyfen Formulations

Few solvent systems allow for dinotefuran to remain in solution for one month at low temperatures. Further, solvent systems which allow for high concentrations of dinotefuran to be dissolved do not typically allow for the solubilization of pyriproxyfen. As shown in Table 1, it has been determined that including a quaternary ammonium salt in the solvent allows for an effective amount of pyriproxyfen to become and remain solubilized, thereby producing a stable formulation. The stability of the formulation is based on the criterion of no crystal formation at 0° F. during a 1 month period.

TABLE 1

Formulation Stability Studies (% are w/w)

| % Dinotefuran | % Pyriproxfen | Solvent System | Quaternary Ammonium Salt | Stable |
|---|---|---|---|---|
| 15 | 1 | Water/Ethyl Lactate/Ethanol | Cetyltrimethylammonium chloride | Yes |
| 15 | 1 | Water/Ethyl Lactate | Cetyltrimethylammonium chloride | Yes |
| 15 | 1 | Water/Ethyl Lactate | tallowalkyltrimethyl ammonium chloride | Yes |
| 15 | 1 | Water/Ethyl Lactate/Ethanol | tallowalkyltrimethyl ammonium chloride | Yes |
| 15 | 1 | Water/Ethyl lactate | Oleyldimethylammonium chloride | Yes |
| 15 | 1 | Water/Ethyl lactate/Ethanol | Oleyldimethylammonium chloride | Yes |
| 15 | 1 | Water/Ethyl lactate/Ethanol | None | No |

It has been determined that the solubility of pyriproxfen in a solution containing dinotefuran can be increased by adding a quaternary amine such as an ammonium chloride salt, for example, cetyltrimethylammonium chloride, tallowalkyltrimethyl ammonium chloride and oleyldimethylammonium chloride compared to a similar formulation without the quaternary ammonium salt. The inclusion of a quaternary ammonium salt up to about 20% results in a formulation which is stable.

Example 4

Formulations containing varying ratios of solvent components were prepared using the procedure discussed in Example 2.

Table 2 contains the composition of the various formulations and demonstrates that the inclusion of a quaternary ammonium salt produces a stable solution containing dinotefuran and pyriproxfen. Stability of the formulation is based on the criterion of no crystal formation at 0° F. during a 1 month period.

TABLE 2

| Solvent System | Ratio of Solvent Components | Quaternary Amines (20%) | % Dinotefuran | % Pyriproxfen | # of Days Stable | Observation |
|---|---|---|---|---|---|---|
| Water/Ethyl lactate/Ethanol | 50/10/40 | Cetrimonium chloride | 15 | 1 | | Precipitation on day 20 |
| Water/Ethyl lactate/Ethanol | 30/40/30 | Cetrimonium chloride | 15 | 1 | 30 | Clear solution |
| Myristamine oxide/Ethyl lactate | 25/75 | Cetrimonium chloride | 15 | 1 | | Precipitation on day 30 |
| Ethyl lactate/Ethanol | 50/50 | Cetrimonium chloride | 15 | 1 | | Precipitation overnight |
| Myristamine oxide/Ethyl lactate | 50/50 | Cetrimonium chloride | 15 | 1 | | Precipitation on day 11 |
| Water/Ethyl lactate | 50/50 | Cetrimonium chloride | 15 | 1 | 42 | Clear solution |
| Water/Ethyl lactate | 25/75 | Cetrimonium chloride | 15 | 1 | 37 | Clear solution |
| Water/Ethyl lactate | 75/25 | Cetrimonium chloride | 15 | 1 | 35 | Clear solution |
| Water/Ethyl lactate/Ethanol | 33.3/33.3/33.3 | Cetrimonium chloride | 15 | 1 | 36 | Clear solution |
| Water/Ethanol | 25/75 | Cetrimonium chloride | 15 | 1 | | Precipitation on day 10 |
| Water/Ethanol | 75/25 | Cetrimonium chloride | 15 | 1 | | Clear solution could not be made |
| Water/Ethyl lactate | 50/50 | Cetrimonium chloride | 15 | 1 | | Precipitation on day 7 |
| Water/Ethyl lactate | 50/50 | Cetrimonium chloride | 18 | 1 | | Precipitation on day 25 |
| Water/Ethyl lactate | 25/75 | Cetrimonium chloride | 18 | 1 | | Precipitation on day 25 |
| Water/Ethyl lactate/Ethanol | 33.3/33.3/33.3 | Cetrimonium chloride | 18 | 1 | | Precipitation on day 7 |
| Water/Ethyl lactate | 50/50 | Cetrimonium chloride | 20 | 1 | | Precipitation on day 14 |
| Water/Ethyl lactate | 25/75 | Cetrimonium chloride | 20 | 1 | | Precipitation on day 20 |
| Water/Ethyl lactate/Ethanol | 33.3/33.3/33.3 | Cetrimonium chloride | 20 | 1 | | Precipitation on day 6 |
| Water/Ethyl lactate | 50/50 | Cetrimonium chloride | 22 | 1 | | Precipitation on day 10 |
| Water/Ethyl lactate | 25/75 | Cetrimonium chloride | 22 | 1 | | Precipitation on day 6 |
| Water/Ethyl lactate/Ethanol | 33.3/33.3/33.3 | Cetrimonium chloride | 22 | 1 | | Precipitation on day 6 |
| Water/Ethanol | 50/50 | Cetrimonium chloride/OP-9 | 15 | 1 | | Precipitation on day 6 |
| Water/Ethanol | 50/50 | Tallowalkyltrimethyl ammonium chloride | 15 | 1 | | Precipitation on day 28 |
| Water/Ethyl lactate | 50/50 | Tallowalkyltrimethyl ammonium chloride | 15 | 1 | 38 | Clear solution |
| Water/Ethanol | 25/75 | Tallowalkyltrimethyl ammonium chloride | 15 | 1 | | Precipitation on day 25 |
| Water/Ethyl lactate | 25/75 | Tallowalkyltrimethyl ammonium chloride | 15 | 1 | 35 | Clear solution |
| Water/Ethyl lactate | 75/25 | Tallowalkyltrimethyl ammonium chloride | 15 | 1 | 20 | Clear solution |
| Water/Ethyl lactate/Ethanol | 50/10/40 | Tallowalkyltrimethyl ammonium chloride | 15 | 1 | 30 | Clear solution |
| Water/Ethyl lactate/Ethanol | 30/40/30 | Tallowalkyltrimethyl ammonium chloride | 15 | 1 | | Precipitation on day 27 |

TABLE 2-continued

| Solvent System | Ratio of Solvent Components | Quaternary Amines (20%) | % Dinotefuran | % Pyriproxfen | # of Days Stable | Observation |
|---|---|---|---|---|---|---|
| Water/Ethyl lactate/Ethanol | 33.3/33.3/33.3 | Tallowalkyltrimethyl ammonium chloride | 15 | 1 | | Precipitation on day 33 |
| Myristamine oxide/Ethyl lactate | 50/50 | Tallowalkyltrimethyl ammonium chloride | 15 | 1 | | Precipitation on day 7 |
| Myristamine oxide/Ethyl lactate | 25/75 | Tallowalkyltrimethyl ammonium chloride | 15 | 1 | | Precipitation on day 27. |
| Ethyl lactate/Ethanol | 50/50 | Tallowalkyltrimethyl ammonium chloride | 15 | 1 | | Precipitation overnight |
| Water/Ethanol | 75/25 | Tallowalkyltrimethyl ammonium chloride | 15 | 1 | | Precipitation on day 4 |
| Water/Ethyl lactate | 50/50 | Tallowalkyltrimethyl ammonium chloride | 18 | 1 | | Precipitation on day 6 |
| Water/Ethyl lactate | 25/75 | Tallowalkyltrimethyl ammonium chloride | 18 | 1 | | Precipitation on day 16 |
| Water/Ethyl lactate | 75/25 | Tallowalkyltrimethyl ammonium chloride | 18 | 1 | | Precipitation on day 6 |
| Water/Ethyl lactate/Ethanol | 33.3/33.3/33.3 | Tallowalkyltrimethyl ammonium chloride | 18 | 1 | | Precipitation on day 16 |
| Water/Ethyl lactate | 50/50 | Tallowalkyltrimethyl ammonium chloride | 20 | 1 | | Precipitation on day 6 |
| Water/Ethyl lactate | 25/75 | Tallowalkyltrimethyl ammonium chloride | 20 | 1 | | Precipitation on day 5 |
| Water/Ethyl lactate | 75/25 | Tallowalkyltrimethyl ammonium chloride | 20 | 1 | | Precipitation on day 6 |
| Water/Ethyl lactate/Ethanol | 33.3/33.3/33.3 | Tallowalkyltrimethyl ammonium chloride | 20 | 1 | | Precipitation on day 6 |
| Water/Ethyl lactate | 50/50 | Tallowalkyltrimethyl ammonium chloride | 22 | 1 | | Precipitation on day 6 |
| Water/Ethyl lactate | 25/75 | Tallowalkyltrimethyl ammonium chloride | 22 | 1 | | Precipitation on day 6 |
| Water/Ethyl lactate | 75/25 | Tallowalkyltrimethyl ammonium chloride | 22 | 1 | | Precipitation on day 6 |
| Water/Ethyl lactate/Ethanol | 33.3/33.3/33.3 | Tallowalkyltrimethyl ammonium chloride | 22 | 1 | | Precipitation on day 6 |
| Water/Ethyl lactate | 50/50 | Oleyldimethylammonium chloride | 15 | 1 | 41 | Clear solution |
| Water/Ethyl lactate | 25/75 | Oleyldimethylammonium chloride | 15 | 1 | 35 | Clear solution |
| Water/Ethyl lactate/Ethanol | 33.3/33.3/33.3 | Oleyldimethylammonium chloride | 15 | 1 | 36 | Clear solution |
| Water/Ethyl lactate/Ethanol | 50/10/40 | Oleyldimethylammonium chloride | 15 | 1 | 15 | Precipitation on day 15 |
| Water/Ethanol | 75/25 | Oleyldimethylammonium chloride | 15 | 1 | | Precipitation on day 29 |
| Water/Ethanol | 25/75 | Oleyldimethylammonium chloride | 15 | 1 | | Precipitation on day 5 |
| Water/Ethyl lactate | 75/25 | Oleyldimethylammonium chloride | 15 | 1 | | Precipitation on day 12 |
| Water/Ethyl lactate/Ethanol | 30/40/30 | Oleyldimethylammonium chloride | 15 | 1 | 30 | Clear solution |
| Ethyl lactate/Ethanol | 50/50 | Oleyldimethylammonium chloride | 15 | 1 | | Precipitation overnight |
| Myristamine oxide/Ethyl lactate | 50/50 | Oleyldimethylammonium chloride | 15 | 1 | | Precipitation on day 7 |
| Myristamine oxide/Ethyl lactate | 25/75 | Oleyldimethylammonium chloride | 15 | 1 | | Precipitation on day 7 |
| Water/Ethyl lactate | 50/50 | Oleyldimethylammonium chloride | 18 | 1 | | Precipitation on day 14 |
| Water/Ethyl lactate | 25/75 | Oleyldimethylammonium chloride | 18 | 1 | | Precipitation on day 16 |
| Water/Ethyl lactate/Ethanol | 33.3/33.3/33.3 | Oleyldimethylammonium chloride | 18 | 1 | | Precipitation on day 6 |
| Water/Ethyl lactate | 50/50 | Oleyldimethylammonium chloride | 20 | 1 | | Precipitation on day 11 |
| Water/Ethyl lactate | 25/75 | Oleyldimethylammonium chloride | 20 | 1 | | Precipitation on day 16 |
| Water/Ethyl lactate/Ethanol | 33.3/33.3/33.3 | Oleyldimethylammonium chloride | 20 | 1 | | Precipitation on day 6 |
| Water/Ethyl lactate | 50/50 | Oleyldimethylammonium chloride | 22 | 1 | | Precipitation on day 14 |

TABLE 2-continued

| Solvent System | Ratio of Solvent Components | Quaternary Amines (20%) | % Dinotefuran | % Pyriproxfen | # of Days Stable | Observation |
|---|---|---|---|---|---|---|
| Water/Ethyl lactate | 25/75 | Oleyldimethylammonium chloride | 22 | 1 | | Precipitation on day 6 |
| Water/Ethyl lactate/Ethanol | 33.3/33.3/33.3 | Oleyldimethylammonium chloride | 22 | 1 | | Precipitation on day 6 |

Example 5

Stability Data for Formulations B C D and E

The following examples of the insecticide composition in accordance with the embodiment of Formulations B, C, D and E were tested for color, appearance and uniformity in various temperatures, some over the duration of four days or more. The composition of these examples and the test results are provided below. The following examples are given for purposes of illustration only and are not intended to be construed in a limiting manner.

Sample Compositions:

FORMULATION B: (% concentration)

| | Composition Numbers | | | | |
|---|---|---|---|---|---|
| Ingredients | 3061-41A | 3061-41B | 3061-41C | 3061-53A | 3061-53B |
| S-1638 | 20.000 | 25.000 | 30.000 | 35.000 | 40.000 |
| n-Methyl pyrrolidone | 73.000 | 68.000 | 63.000 | 58.000 | 53.000 |
| Agsolex 8 | 6.000 | 6.000 | 6.000 | 6.000 | 6.000 |
| Nylar | 1.000 | 1.000 | 1.000 | 1.000 | 1.000 |
| | | | TS# 12839 | TS#12848 | |

FORMULATION C:

(% concentration)

| | Composition Numbers | | | | | |
|---|---|---|---|---|---|---|
| Ingredients | 3061-62A | 3061-62B | 3061-62C | 3061-62D | 3061-62E | 3061-62F |
| S-1638 | 30.00 | 30.00 | 30.00 | 30.00 | 30.00 | 30.00 |
| Nylar | 1.50 | 2.00 | 2.50 | 3.00 | 3.50 | 4.00 |
| Agsolex 8 | 6.00 | 6.00 | 6.00 | 6.00 | 6.00 | 6.00 |
| n-Methyl pyrrolidone | 62.50 | 62.00 | 61.50 | 61.00 | 60.50 | 60.00 |
| | TS#12840 | TS#12841 | TS#12842 | TS#12843 | TS#12844 | TS#12845 |

| | Composition Numbers | | | | | |
|---|---|---|---|---|---|---|
| Ingredients | 3061-62G | 3061-62H | 3061-62I | 3061-62J | 3061-62K | 3061-62L |
| S-1638 | 30.00 | 30.00 | 30.00 | 30.00 | 30.00 | 30.00 |
| Nylar | 4.50 | 5.00 | 5.50 | 6.00 | 6.50 | 7.00 |
| Agsolex 8 | 6.00 | 6.00 | 6.00 | 6.00 | 6.001 | 6.00 |
| n-Methl pyrrolidone | 59.50 | 59.00 | 58.50 | 58.00 | 57.50 | 57.00 |
| | TS#12846 | TS#12847 | | | | |

FORMULATION D:

(% concentration)

| | Composition Numbers | | | | | |
|---|---|---|---|---|---|---|
| Ingredients | 3061-63A | 3061-63B | 3061-63C | 3061-63D | 3061-63E | 3061-63F |
| S-1638 | 35.00 | 35.00 | 35.00 | 35.00 | 35.00 | 35.00 |
| Nylar | 1.50 | 2.00 | 2.50 | 3.00 | 3.50 | 4.00 |
| Agsolex 8 | 6.00 | 6.00 | 6.00 | 6.00 | 6.00 | 6.00 |
| n-Methyl pyrrolidone | 57.50 | 57.00 | 56.50 | 56.00 | 55.50 | 55.00 |
| | TS#12849 | TS#12850 | TS#12851 | TS#12852 | TS#12853 | TS#12854 |

-continued

FORMULATION D:
(% concentration)

| Ingredients | Composition Numbers | | | | | |
|---|---|---|---|---|---|---|
| | 3061-63G | 3061-63H | 3061-63I | 3061-63J | 3061-63K | 3061-63L |
| S-1638 | 35.00 | 35.00 | 35.00 | 35.00 | 35.00 | 35.00 |
| Nylar | 4.50 | 5.00 | 5.50 | 6.00 | 6.50 | 7.00 |
| Agsolex 8 | 6.00 | 6.00 | 6.00 | 6.00 | 6.00 | 6.00 |
| n-Methyl pyrrolidone | 54.50 | 54.00 | 53.50 | 53.00 | 52.50 | 52.00 |
| | TS#12855 | TS#12856 | | | | |

FORMULATION E: (% concentration)

| Ingredients | Composition Numbers | | |
|---|---|---|---|
| | 3061-55A | 3061-55B | 3061-55K |
| S-1638 | 20.000 | 25.000 | 20.000 |
| n-Methyl pyrrolidone | 54.000 | 51.000 | 45.000 |
| DI H2O | 18.000 | 16.000 | 27.000 |
| Agsolex 8 | 6.000 | 6.000 | 6.000 |
| Nylar | 2.000 | 2.000 | 2.000 |

S-1638 is dinotefuran and Agsolex 8 is N-octyl pyrrolidone. Pyriproxyfen is also known as Nylar.

Test Results:

Table 3A shows the results of the stability testing at room temperature.

TABLE 3A

| | Room Temperature | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-41A | | | | | | | | | | |
| Color | sl yellow | sl yellow | sl yellow | sl yellow | sl yellow | sl yellow | sl yellow | sl yellow | sl yellow | sl yellow |
| Appearance | clear | clear | clear | clear | clear | clear | clear | clear | clear | clear |
| Uniform? | yes | yes | yes | yes | yes | yes | yes | yes | yes | yes |
| Comp #3061-41B | | | | | | | | | | |
| Color | sl yellow | sl yellow | sl yellow | sl yellow | sl yellow | sl yellow | sl yellow | sl yellow | sl yellow | sl yellow |
| Appearance | clear | clear | clear | clear | clear | clear | clear | clear | clear | clear |
| Uniform? | yes | yes | yes | yes | yes | yes | yes | yes | yes | yes |
| Comp #3061-41B | | | | | | | | | | |
| Color | sl yellow | sl yellow | sl yellow | sl yellow | sl yellow | sl yellow | sl yellow | sl yellow | sl yellow | sl yellow |
| Appearance | clear | clear | clear | clear | clear | clear | clear | clear | clear | clear |
| Uniform? | yes | yes | yes | yes | yes | yes | yes | yes | yes | yes |
| Comp # 3061-53A | | | | | | | | | | |
| Color | sl yellow | sl yellow | sl yellow | sl yellow | sl yellow | sl yellow | sl yellow | sl yellow | sl yellow | |
| Appearance | clear | clear | clear | clear | clear | clear | clear | clear | clear | |
| Uniform? | yes | yes | yes | yes | yes | yes | yes | yes | yes | |
| Comp # 3061-53B | | | | | | | | | | |
| Color | sl yellow | sl yellow | sl yellow | sl yellow | sl yellow | sl yellow | sl yellow | sl yellow | | |
| Appearance | clear | clear | clear | clear | clear | clear | clear | clear | | |
| Uniform? | yes | yes | yes | yes | yes | yes | yes | yes | | |

TABLE 3A-continued

| | Room Temperature | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-55A | | | | | | | | | | |
| Color Appearance Uniform? | sl yellow clear yes | sl yellow clear yes | sl yellow clear yes | sl yellow clear yes | sl yellow clear yes | sl yellow clear yes | sl yellow clear yes | sl yellow clear yes | | |
| Comp # 3061-55B | | | | | | | | | | |
| Color Appearance Uniform? | sl yellow clear yes | sl yellow clear yes | sl yellow clear yes | sl yellow clear yes | sl yellow clear yes | sl yellow clear yes | sl yellow clear yes | sl yellow clear yes | | |
| Comp # 3061-55K | | | | | | | | | | |
| Color Appearance Uniform? | sl yellow clear yes | sl yellow clear yes | sl yellow clear yes | sl yellow clear yes | sl yellow clear yes | sl yellow clear yes | sl yellow clear yes | sl yellow clear yes | | |
| Comp # 3061-62A | | | | | | | | | | |
| Color Appearance Uniform? | sl yellow clear yes | sl yellow clear yes | | | | | | | | |
| Comp # 3061-62B | | | | | | | | | | |
| Color Appearance Uniform? | sl yellow clear yes | sl yellow clear yes | | | | | | | | |
| Comp # 3061-62C | | | | | | | | | | |
| Color Appearance Uniform? | sl yellow clear yes | sl yellow clear yes | | | | | | | | |
| Comp # 3061-62D | | | | | | | | | | |
| Color Appearance Uniform? | sl yellow clear yes | sl yellow clear yes | | | | | | | | |
| Comp # 3061-62F | | | | | | | | | | |
| Color Appearance Uniform? | sl yellow clear yes | sl yellow clear yes | | | | | | | | |
| Comp # 3061-62G | | | | | | | | | | |
| Color Appearance Uniform? | sl yellow clear yes | sl yellow clear yes | | | | | | | | |
| Comp # 3061-62H | | | | | | | | | | |
| Color Appearance Uniform? | sl yellow clear yes | sl yellow clear yes | | | | | | | | |
| Comp # 3061-62I | | | | | | | | | | |
| Color Appearance Uniform? | sl yellow clear yes | sl yellow clear yes | | | | | | | | |
| Comp # 3061-62J | | | | | | | | | | |
| Color Appearance Uniform? | sl yellow clear yes | sl yellow clear yes | | | | | | | | |

TABLE 3A-continued

| | Room Temperature | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-62K | | | | | | | | | | |
| Color Appearance Uniform? | sl yellow clear yes | sl yellow clear yes | | | | | | | | |
| Comp # 3061-62L | | | | | | | | | | |
| Color Appearance Uniform? | sl yellow clear yes | sl yellow clear yes | | | | | | | | |
| Comp # 3061-63A | | | | | | | | | | |
| Color Appearance Uniform? | sl yellow clear yes | sl yellow clear yes | | | | | | | | |
| Comp # 3061-63B | | | | | | | | | | |
| Color Appearance Uniform? | sl yellow clear yes | sl yellow clear yes | | | | | | | | |
| Comp # 3061-63C | | | | | | | | | | |
| Color Appearance Uniform? | sl yellow clear yes | sl yellow clear yes | | | | | | | | |
| Comp # 3061-63D | | | | | | | | | | |
| Color Appearance Uniform? | sl yellow clear yes | sl yellow clear yes | | | | | | | | |
| Comp # 3061-63E | | | | | | | | | | |
| Color Appearance Uniform? | sl yellow clear yes | sl yellow clear yes | | | | | | | | |
| Comp # 3061-63F | | | | | | | | | | |
| Color Appearance Uniform? | sl yellow clear yes | sl yellow clear yes | | | | | | | | |
| Comp # 3061-63G | | | | | | | | | | |
| Color Appearance Uniform? | sl yellow clear yes | sl yellow clear yes | | | | | | | | |
| Comp # 3061-63H | | | | | | | | | | |
| Color Appearance Uniform? | sl yellow clear yes | sl yellow clear yes | | | | | | | | |
| Comp # 3061-63I | | | | | | | | | | |
| Color Appearance Uniform? | sl yellow clear yes | sl yellow clear yes | | | | | | | | |
| Comp # 3061-63J | | | | | | | | | | |
| Color Appearance Uniform? | sl yellow clear yes | sl yellow clear yes | | | | | | | | |

TABLE 3A-continued

| | Room Temperature | | | | | | | | |
|---|---|---|---|---|---|---|---|---|---|
| | INITIAL | Day 4 | Day 7 | Day 10 | Day 14 | Day 17 | Day 20 | Day 24 | Day 27 | Day 30 |

Comp # 3061-63K

| Color Appearance | sl yellow clear | sl yellow clear | | | | | | | | |
|---|---|---|---|---|---|---|---|---|---|---|
| Uniform? | yes | yes | | | | | | | | |

Comp # 3061-63L

| Color Appearance | sl yellow clear | sl yellow clear | | | | | | | | |
|---|---|---|---|---|---|---|---|---|---|---|
| Uniform? | yes | yes | | | | | | | | |

Table 3B shows the results of the stability testing at 4° C.

TABLE 3B

| | 4° C. | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |

Comp # 3061-41A

| Color Appearance | sl yellow clear | sl yellow clear | sl yellow clear | sl yellow clear | sl yellow clear | sl yellow clear | sl yellow clear | sl yellow clear | sl yellow clear | sl yellow clear |
|---|---|---|---|---|---|---|---|---|---|---|
| Uniform? | yes | yes | yes | yes | yes | yes | yes | yes | yes | yes |

Comp #3061-41B

| Color Appearance | sl yellow clear | sl yellow clear | sl yellow clear | sl yellow clear | sl yellow clear | sl yellow clear | sl yellow clear | sl yellow clear | sl yellow clear | sl yellow clear |
|---|---|---|---|---|---|---|---|---|---|---|
| Uniform? | yes | yes | yes | yes | yes | yes | yes | yes | yes | yes |

Comp #3061-41B

| Color Appearance | sl yellow clear | sl yellow clear | sl yellow clear | sl yellow clear | sl yellow clear | sl yellow clear | sl yellow clear | sl yellow clear | sl yellow clear | sl yellow clear |
|---|---|---|---|---|---|---|---|---|---|---|
| Uniform? | yes | yes | yes | yes | yes | yes | yes | yes | yes | yes |

Comp # 3061-53A

| Color Appearance | sl yellow clear | sl yellow clear | sl yellow clear | sl yellow clear | sl yellow clear | sl yellow clear | sl yellow clear | sl yellow clear | sl yellow clear | |
|---|---|---|---|---|---|---|---|---|---|---|
| Uniform? | yes | yes | yes | yes | yes | yes | yes | yes | yes | |

Comp # 3061-53B

| Color Appearance | sl yellow clear | sl yellow clear | sl yellow clear | sl yellow clear | sl yellow clear | sl yellow clear | sl yellow clear | sl yellow clear | sl yellow clear | |
|---|---|---|---|---|---|---|---|---|---|---|
| Uniform? | yes | yes | yes | yes | yes | yes | yes | yes | yes | |

Comp # 3061-55A

| Color Appearance | sl yellow clear | sl yellow clear | sl yellow clear | sl yellow clear | sl yellow clear | sl yellow clear | sl yellow clear | sl yellow clear | | |
|---|---|---|---|---|---|---|---|---|---|---|
| Uniform? | yes | yes | yes | yes | yes | yes | yes | yes | | |

Comp # 3061-55B

| Color Appearance | sl yellow clear | sl yellow clear | sl yellow clear | sl yellow clear | sl yellow clear | sl yellow clear | sl yellow clear | sl yellow Clear crystals | | |
|---|---|---|---|---|---|---|---|---|---|---|
| Uniform? | yes | yes | yes | yes | yes | yes | yes | | | |

Comp # 3061-55K

| Color Appearance | sl yellow clear | sl yellow clear | sl yellow clear | sl yellow clear | sl yellow clear | sl yellow clear | sl yellow clear crystals | sl yellow clear crystals | | |
|---|---|---|---|---|---|---|---|---|---|---|
| Uniform? | yes | yes | yes | yes | yes | yes | | | | |

TABLE 3B-continued

| | 4° C. | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-62A | | | | | | | | | | |
| Color Appearance Uniform? | sl yellow clear yes | sl yellow clear yes | | | | | | | | |
| Comp # 3061-62B | | | | | | | | | | |
| Color Appearance Uniform? | sl yellow clear yes | sl yellow clear yes | | | | | | | | |
| Comp # 3061-62C | | | | | | | | | | |
| Color Appearance Uniform? | sl yellow clear yes | sl yellow clear yes | | | | | | | | |
| Comp # 3061-62D | | | | | | | | | | |
| Color Appearance Uniform? | sl yellow clear yes | sl yellow clear yes | | | | | | | | |
| Comp # 3061-62F | | | | | | | | | | |
| Color Appearance Uniform? | sl yellow clear yes | sl yellow clear yes | | | | | | | | |
| Comp # 3061-62G | | | | | | | | | | |
| Color Appearance Uniform? | sl yellow clear yes | sl yellow clear yes | | | | | | | | |
| Comp # 3061-62H | | | | | | | | | | |
| Color Appearance Uniform? | sl yellow clear yes | sl yellow clear yes | | | | | | | | |
| Comp # 3061-62I | | | | | | | | | | |
| Color Appearance Uniform? | sl yellow clear yes | sl yellow clear yes | | | | | | | | |
| Comp # 3061-62J | | | | | | | | | | |
| Color Appearance Uniform? | sl yellow clear yes | sl yellow clear yes | | | | | | | | |
| Comp # 3061-62K | | | | | | | | | | |
| Color Appearance Uniform? | sl yellow clear yes | sl yellow clear yes | | | | | | | | |
| Comp # 3061-62L | | | | | | | | | | |
| Color Appearance Uniform? | sl yellow clear yes | sl yellow clear yes | | | | | | | | |
| Comp # 3061-63A | | | | | | | | | | |
| Color Appearance Uniform? | sl yellow clear yes | sl yellow clear yes | | | | | | | | |

TABLE 3B-continued

| | 4° C. | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-63B | | | | | | | | | | |
| Color Appearance | sl yellow clear | sl yellow clear | | | | | | | | |
| Uniform? | yes | yes | | | | | | | | |
| Comp # 3061-63C | | | | | | | | | | |
| Color Appearance | sl yellow clear | sl yellow clear | | | | | | | | |
| Uniform? | yes | yes | | | | | | | | |
| Comp # 3061-63D | | | | | | | | | | |
| Color Appearance | sl yellow clear | sl yellow clear | | | | | | | | |
| Uniform? | yes | yes | | | | | | | | |
| Comp # 3061-63E | | | | | | | | | | |
| Color Appearance | sl yellow clear | sl yellow clear | | | | | | | | |
| Uniform? | yes | yes | | | | | | | | |
| Comp # 3061-63F | | | | | | | | | | |
| Color Appearance | sl yellow clear | sl yellow clear | | | | | | | | |
| Uniform? | yes | yes | | | | | | | | |
| Comp # 3061-63G | | | | | | | | | | |
| Color Appearance | sl yellow clear | sl yellow clear | | | | | | | | |
| Uniform? | yes | yes | | | | | | | | |
| Comp # 3061-63H | | | | | | | | | | |
| Color Appearance | sl yellow clear | sl yellow clear | | | | | | | | |
| Uniform? | yes | yes | | | | | | | | |
| Comp # 3061-63I | | | | | | | | | | |
| Color Appearance | sl yellow clear | sl yellow clear | | | | | | | | |
| Uniform? | yes | yes | | | | | | | | |
| Comp # 3061-63J | | | | | | | | | | |
| Color Appearance | sl yellow clear | sl yellow clear | | | | | | | | |
| Uniform? | yes | yes | | | | | | | | |
| Comp # 3061-63K | | | | | | | | | | |
| Color Appearance | sl yellow clear | sl yellow clear | | | | | | | | |
| Uniform? | yes | yes | | | | | | | | |

TABLE 3B-continued

| | 4° C. | | | | | | | | |
|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-63L | | | | | | | | | | |
| Color | sl yellow | sl yellow | | | | | | | | |
| Appearance | clear | clear | | | | | | | | |
| Uniform? | yes | yes | | | | | | | | |

Table 3C shows the results of the stability testing under freeze (0° F.)/thaw (F/T) conditions.

TABLE 3C

| | F/T | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-41A | | | | | | | | | | |
| Color | sl yellow | sl yellow | sl yellow | sl yellow | sl yellow | sl yellow | sl yellow | sl yellow | sl yellow | sl yellow |
| Appearance | clear | clear | clear | clear | clear | clear | clear | clear | clear | clear |
| Uniform? | yes | yes | yes | yes | yes | yes | yes | yes | yes | yes |
| Comp #3061-41B | | | | | | | | | | |
| Color | sl yellow | sl yellow | sl yellow | sl yellow | sl yellow | sl yellow | sl yellow | sl yellow | sl yellow | sl yellow |
| Appearance | clear | clear | clear | clear | clear | clear | clear | clear | clear | clear |
| Uniform? | yes | yes | yes | yes | yes | yes | yes | yes | yes | yes |
| Comp # 3061-41B | | | | | | | | | | |
| Color | sl yellow | sl yellow | sl yellow | sl yellow | sl yellow | sl yellow | sl yellow | sl yellow | sl yellow | sl yellow |
| Appearance | clear | clear | clear | clear | clear | clear | clear | clear | clear | clear |
| Uniform? | yes | yes | yes | yes | yes | yes | yes | yes | yes | yes |
| Comp # 3061-53A | | | | | | | | | | |
| Color | sl yellow | sl yellow | sl yellow | sl yellow | sl yellow | sl yellow | sl yellow | sl yellow | sl yellow | |
| Appearance | clear | clear | clear | clear | clear | clear | clear | clear | clear | |
| Uniform? | yes | yes | yes | yes | yes | yes | yes | yes | yes | |
| Comp # 3061-53B | | | | | | | | | | |
| Color | sl yellow | sl yellow | sl yellow | sl yellow | sl yellow | sl yellow | sl yellow | sl yellow | sl yellow | |
| Appearance | clear | clear | clear | cloudy | clear | clear | clear | clear | clear | |
| Uniform? | yes | yes | yes | yes | crystals | crystals | crystals | crystals | crystals | |
| Comp # 3061-55A | | | | | | | | | | |
| Color | sl yellow | sl yellow | sl yellow | sl yellow | sl yellow | sl yellow | sl yellow | sl yellow | | |
| Appearance | clear | clear | clear | clear | clear | clear | clear | clear | | |
| Uniform? | yes | yes | yes | yes | yes | yes | yes | yes | | |
| Comp # 3061-55B | | | | | | | | | | |
| Color | sl yellow | sl yellow | sl yellow | sl yellow | sl yellow | sl yellow | sl yellow | sl yellow | | |
| Appearance | clear | clear | clear | clear | clear | clear | clear | clear | | |
| Uniform? | yes | yes | yes | yes | yes | crystals | crystals | crystals | | |
| Comp # 3061-55K | | | | | | | | | | |
| Color | sl yellow | sl yellow | sl yellow | sl yellow | sl yellow | sl yellow | sl yellow | sl yellow | | |
| Appearance | clear | clear | clear | clear | clear | clear | clear | clear | | |
| Uniform? | yes | yes | yes | crystals | crystals | crystals | crystals | crystals | | |
| Comp # 3061-62A | | | | | | | | | | |
| Color | sl yellow | sl yellow | | | | | | | | |
| Appearance | clear | clear | | | | | | | | |
| Uniform? | yes | yes | | | | | | | | |

TABLE 3C-continued

| | F/T | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-62B | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62C | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62D | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62F | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62G | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62H | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62I | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62J | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62K | | | | | | | | | | |
| Color | sl yellow | sl yellow | | | | | | | | |
| Appearance | clear | clear | | | | | | | | |
| Uniform? | yes | yes | | | | | | | | |
| Comp # 3061-62L | | | | | | | | | | |
| Color | sl yellow | sl yellow | | | | | | | | |
| Appearance | clear | clear | | | | | | | | |
| Uniform? | yes | yes | | | | | | | | |
| Comp # 3061-63A | | | | | | | | | | |
| Color | sl yellow | sl yellow | | | | | | | | |
| Appearance | clear | clear | | | | | | | | |
| Uniform? | yes | yes | | | | | | | | |
| Comp # 3061-63B | | | | | | | | | | |
| Color | sl yellow | sl yellow | | | | | | | | |
| Appearance | clear | clear | | | | | | | | |
| Uniform? | yes | yes | | | | | | | | |

TABLE 3C-continued

| | F/T | | | | | | | | | |
|---|---|---|---|---|---|---|---|---|---|---|
| | INITIAL | Day 4 | Day 7 | Day 10 | Day 14 | Day 17 | Day 20 | Day 24 | Day 27 | Day 30 |
| Comp # 3061-63C | | | | | | | | | | |
| Color Appearance | sl yellow clear | sl yellow clear | | | | | | | | |
| Uniform? | yes | yes | | | | | | | | |
| Comp # 3061-63D | | | | | | | | | | |
| Color Appearance | sl yellow clear | sl yellow clear | | | | | | | | |
| Uniform? | yes | yes | | | | | | | | |
| Comp # 3061-63E | | | | | | | | | | |
| Color Appearance | sl yellow clear | sl yellow clear | | | | | | | | |
| Uniform? | yes | yes | | | | | | | | |
| Comp # 3061-63F | | | | | | | | | | |
| Color Appearance | sl yellow clear | sl yellow clear | | | | | | | | |
| Uniform? | yes | yes | | | | | | | | |
| Comp # 3061-63G | | | | | | | | | | |
| Color Appearance | sl yellow clear | sl yellow clear | | | | | | | | |
| Uniform? | yes | yes | | | | | | | | |
| Comp # 3061-63H | | | | | | | | | | |
| Color Appearance | sl yellow clear | sl yellow clear | | | | | | | | |
| Uniform? | yes | yes | | | | | | | | |
| Comp # 3061-63I | | | | | | | | | | |
| Color Appearance | sl yellow clear | sl yellow clear | | | | | | | | |
| Uniform? | yes | yes | | | | | | | | |
| Comp # 3061-63J | | | | | | | | | | |
| Color Appearance | sl yellow clear | sl yellow clear | | | | | | | | |
| Uniform? | yes | yes | | | | | | | | |
| Comp # 3061-63K | | | | | | | | | | |
| Color Appearance | sl yellow clear | sl yellow clear | | | | | | | | |
| Uniform? | yes | yes | | | | | | | | |
| Comp # 3061-63L | | | | | | | | | | |
| Color Appearance | sl yellow clear | sl yellow clear | | | | | | | | |
| Uniform? | yes | yes | | | | | | | | |

Example 6

Stability Data for Formulations G and H

The following examples of the insecticide composition in accordance with the embodiment of Formulations G and H were tested for uniformity under freeze/thaw conditions over a duration of four weeks. The composition of these examples and the test results are provided below. The following examples are given for purposes of illustration only and are not intended to be construed in a limiting manner.

TABLE 4A

Series A Compositions
Compositions are given in percent by weight.

|  | Positive Control | Comp #1 | Comp #2 | Comp #3 | Comp #4 | Comp #5 | Comp #6 | Comp #7 | Comp #8 | Comp #9 |
|---|---|---|---|---|---|---|---|---|---|---|
| Dinoterfuran | 20 | 20 | 20 | 20 | 20 | 20 | 20 | 20 | 20 | 20 |
| Nylar | 3 | 3 | 3 | 3 | 3 | 3 | 3 | 3 | 3 | 3 |
| NMP | 26 | 30 | 35 | 40 | 45 | 26 | 30 | 35 | 40 | 45 |
| NOP | 3 | 3 | 3 | 3 | 3 | 6 | 6 | 6 | 6 | 6 |
| Propylene carbonate | 48 | 44 | 39 | 34 | 29 | 45 | 41 | 36 | 31 | 26 |
| Crystals? | YES | YES | NO | NO | NO | YES | YES | NO | NO | NO |

TABLE 4B

Series B Compositions
Compositions are given in percent by weight.

|  | Positive Control | Comp #1 | Comp #2 | Comp #3 | Comp #4 | Comp #5 | Comp #6 | Comp #7 | Comp #8 | Comp #9 |
|---|---|---|---|---|---|---|---|---|---|---|
| Dinoterfuran | 22 | 22 | 22 | 22 | 22 | 22 | 22 | 22 | 22 | 22 |
| Nylar | 3 | 3 | 3 | 3 | 3 | 3 | 3 | 3 | 3 | 3 |
| NMP | 26 | 30 | 35 | 40 | 45 | 26 | 30 | 35 | 40 | 45 |
| NOP | 3 | 3 | 3 | 3 | 3 | 6 | 6 | 6 | 6 | 6 |
| Propylene carbonate | 46 | 42 | 37 | 32 | 27 | 43 | 39 | 34 | 29 | 24 |
| Crystals? | YES | YES | YES | NO | NO | YES | YES | NO | NO | NO |

TABLE 4C

Series C Compositions
Compositions are given in percent by weight.

|  | Positive Control | Comp #1 | Comp #2 | Comp #3 | Comp #4 | Comp #5 | Comp #6 | Comp #7 | Comp #8 | Comp #9 |
|---|---|---|---|---|---|---|---|---|---|---|
| Dinoterfuran | 25 | 25 | 25 | 25 | 25 | 25 | 25 | 25 | 25 | 25 |
| Nylar | 3 | 3 | 3 | 3 | 3 | 3 | 3 | 3 | 3 | 3 |
| NMP | 26 | 30 | 35 | 40 | 45 | 26 | 30 | 35 | 40 | 45 |
| NOP | 3 | 3 | 3 | 3 | 3 | 6 | 6 | 6 | 6 | 6 |
| Propylene carbonate | 43 | 39 | 34 | 29 | 24 | 40 | 36 | 31 | 26 | 21 |
| Crystals? | YES | YES | YES | YES | NO | YES | YES | YES | YES | NO |

TABLE 4D

Series D Compositions
Compositions are given in percent by weight.

|  | Positive Control | Comp #1 | Comp #2 | Comp #3 | Comp #4 | Comp #5 | Comp #6 | Comp #7 | Comp #8 | Comp #9 |
|---|---|---|---|---|---|---|---|---|---|---|
| Dinoterfuran | 30 | 30 | 30 | 30 | 30 | 30 | 30 | 30 | 30 | 30 |
| Nylar | 3 | 3 | 3 | 3 | 3 | 3 | 3 | 3 | 3 | 3 |
| NMP | 26 | 30 | 35 | 40 | 45 | 26 | 30 | 35 | 40 | 45 |
| NOP | 3 | 3 | 3 | 3 | 3 | 6 | 6 | 6 | 6 | 6 |
| Propylene carbonate | 38 | 34 | 29 | 24 | 19 | 35 | 31 | 26 | 21 | 16 |
| Crystals? | YES | YES | YES | YES | YES | YES | YES | YES | YES | YES |

TABLE 4E

Series E Compositions
Compositions are given in percent by weight.

| | Positive Control | Comp #1 | Comp #2 | Comp #3 | Comp #4 | Comp #5 | Comp #6 | Comp #7 | Comp #8 | Comp #9 |
|---|---|---|---|---|---|---|---|---|---|---|
| Dinoterfuran | 20 | 20 | 20 | 20 | 20 | 20 | 20 | 20 | 20 | 20 |
| Nylar | 1 | 1 | 1 | 1 | 1 | 1 | 1 | 1 | 1 | 1 |
| NMP | 28 | 32 | 37 | 42 | 47 | 28 | 32 | 37 | 42 | 47 |
| NOP | 3 | 3 | 3 | 3 | 3 | 6 | 6 | 6 | 6 | 6 |
| Propylene carbonate | 48 | 44 | 39 | 34 | 29 | 45 | 41 | 36 | 31 | 26 |
| Crystals? | YES | NO | NO | NO | NO | YES | NO | NO | NO | NO |

TABLE 4F

Series F Compositions
Compositions are given in percent by weight.

| | Comp #1 | Comp #2 | Comp #3 | Comp #4 | Comp #5 | Comp #6 | Comp #7 | Comp #8 | Comp #9 | Comp #10 |
|---|---|---|---|---|---|---|---|---|---|---|
| Dinoterfuran | 22 | 22 | 22 | 22 | 22 | 22 | 22 | 22 | 22 | 22 |
| Nylar | 1 | 1 | 1 | 1 | 1 | 1 | 1 | 1 | 1 | 1 |
| NMP | 28 | 32 | 37 | 42 | 47 | 28 | 32 | 37 | 42 | 47 |
| NOP | 3 | 3 | 3 | 3 | 3 | 6 | 6 | 6 | 6 | 6 |
| Propylene carbonate | 46 | 42 | 37 | 32 | 27 | 43 | 39 | 34 | 29 | 24 |
| Crystals? | YES | YES | NO | NO | NO | YES | YES | NO | NO | NO |

TABLE 4G

Series G Compositions
Compositions are given in percent by weight.

| | Comp #1 | Comp #2 | Comp #3 | Comp #4 | Comp #5 | Comp #6 | Comp #7 | Comp #8 | Comp #9 | Comp #10 |
|---|---|---|---|---|---|---|---|---|---|---|
| Dinoterfuran | 25 | 25 | 25 | 25 | 25 | 25 | 25 | 25 | 25 | 25 |
| Nylar | 1 | 1 | 1 | 1 | 1 | 1 | 1 | 1 | 1 | 1 |
| NMP | 28 | 32 | 37 | 42 | 47 | 28 | 32 | 37 | 42 | 47 |
| NOP | 3 | 3 | 3 | 3 | 3 | 6 | 6 | 6 | 6 | 6 |
| Propylene carbonate | 43 | 39 | 34 | 29 | 24 | 40 | 36 | 31 | 26 | 21 |
| Crystals? | YES | YES | YES | NO | NO | YES | YES | YES | YES | NO |

TABLE 4H

Series H Compositions
Compositions are given in percent by weight.

| | Comp #1 | Comp #2 | Comp #3 | Comp #4 | Comp #5 | Comp #6 | Comp #7 | Comp #8 | Comp #9 | Comp #10 |
|---|---|---|---|---|---|---|---|---|---|---|
| Dinoterfuran | 30 | 30 | 30 | 30 | 30 | 30 | 30 | 30 | 30 | 30 |
| Nylar | 1 | 1 | 1 | 1 | 1 | 1 | 1 | 1 | 1 | 1 |
| NMP | 28 | 32 | 37 | 42 | 47 | 28 | 32 | 37 | 42 | 47 |
| NOP | 3 | 3 | 3 | 3 | 3 | 6 | 6 | 6 | 6 | 6 |
| Propylene carbonate | 38 | 34 | 29 | 24 | 19 | 35 | 31 | 26 | 21 | 16 |
| Crystals? | YES | YES | YES | YES | YES | YES | YES | YES | YES | YES |

It can be seen that insecticides in accordance with the invention can remain liquids, without readily observable precipitation (e.g., visible crystal formation), at room temperature, preferably less than about 4° C. and more preferably under about 0° C. for more than 4 days, preferably more than 28 days.

It will thus be seen that the objects set forth above, among those made apparent from the preceding description, are efficiently attained and, since certain changes may be made in carrying out the above method and in the formulations set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall there between. Particularly it is to be understood that in said claims, ingredients or compounds recited in the singular are intended to include compatible mixtures of such ingredients wherever the sense permits.

What is claimed is:

1. A liquid insecticide formulated by combining components, comprising, by weight:
   about 18% to 26% dinotefuran;
   about 1% to 7% pyriproxyfen;
   about 30% to 38% propylene carbonate;
   about 30% to 94% N-methyl pyrrolidone; and
   about 0.1% to 8% N-octyl pyrrolidone;
   the liquid formulated so that the dinotefuran and pyriproxyfen remain in solution for over twenty-eight days when stored at a temperature under 4° C.

2. The insecticide of claim 1, comprising about 20% to 25% by weight dinotefuran.

3. The insecticide of claim 1, comprising about 2% to 4% by weight pyriproxyfen.

4. The insecticide of claim 1, comprising about 34% to 36% by weight N-methyl pyrrolidone.

5. The insecticide of claim 1, comprising about 5% to 7% by weight N-octyl pyrrolidone.

6. The insecticide of claim 1, comprising about 2% to 4% by weight pyriproxyfen, about 30% to 48% N-methyl pyrrolidone, and about 3% to 8% by weight of N-octyl pyrrolidone.

7. The insecticide of claim 1, comprising about 21% to 23% by weight dinotefuran, about 2% to 4% by weight pyriproxyfen, about 33% to 35% by weight propylene carbonate, about 34% to 36% by weight N-methyl pyrrolidone, and about 5% to 7% by weight N-octyl pyrrolidone.

8. A method of treating house pets, comprising applying an insecticidally effective amount of the insecticide of claim 1 onto the pet.

9. The method of claim 8, wherein the insecticide is applied to the pet as a topical spot on the pet.

* * * * *